(12) United States Patent
Hamada et al.

(10) Patent No.: US 8,821,566 B2
(45) Date of Patent: Sep. 2, 2014

(54) ALLOY FOR MEDICAL USE AND MEDICAL DEVICE

(75) Inventors: Kenichi Hamada, Tokushima (JP); Eiichi Honda, Tokushima (JP); Kenzo Asaoka, Tokushima (JP); Midori Yoshida, Tokushima (JP)

(73) Assignee: The University of Tokushima, Tokushima (JP)

( * ) Notice: Subject to any disclaimer, the term of this patent is extended or adjusted under 35 U.S.C. 154(b) by 0 days.

(21) Appl. No.: 13/138,245

(22) PCT Filed: Jan. 22, 2010

(86) PCT No.: PCT/JP2010/050789
§ 371 (c)(1),
(2), (4) Date: Oct. 6, 2011

(87) PCT Pub. No.: WO2010/084948
PCT Pub. Date: Jul. 29, 2010

(65) Prior Publication Data
US 2012/0035632 A1  Feb. 9, 2012

(30) Foreign Application Priority Data

Jan. 24, 2009 (JP) ................. 2009-013725

(51) Int. Cl.
| | |
|---|---|
| *A61F 2/06* | (2013.01) |
| *C22F 1/14* | (2006.01) |
| *A61L 31/18* | (2006.01) |
| *A61L 31/02* | (2006.01) |
| *G01R 33/28* | (2006.01) |
| *C22C 5/02* | (2006.01) |
| *A61N 1/375* | (2006.01) |
| *A61F 2/82* | (2013.01) |
| *A61N 1/08* | (2006.01) |

(52) U.S. Cl.
CPC ............... *A61L 31/022* (2013.01); *C22F 1/14* (2013.01); *A61L 31/18* (2013.01); *A61N 1/375* (2013.01); *G01R 33/288* (2013.01); *A61F 2/82* (2013.01); *C22C 5/02* (2013.01); *A61N 2001/086* (2013.01)
USPC .......................................... 623/1.34; 148/678

(58) Field of Classification Search
USPC ........................................ 623/1.34; 148/678
See application file for complete search history.

(56) References Cited

U.S. PATENT DOCUMENTS

| | | | |
|---|---|---|---|
| 2005/0033407 A1* | 2/2005 | Weber et al. ................. | 623/1.15 |
| 2005/0121120 A1* | 6/2005 | Van Dijk et al. .............. | 148/678 |

FOREIGN PATENT DOCUMENTS

| | | |
|---|---|---|
| JP | 2004-035998 A | 2/2004 |
| JP | 2004-505651 A | 2/2004 |

(Continued)

OTHER PUBLICATIONS

International Search Report mailed on Apr. 20, 2010.

(Continued)

*Primary Examiner* — Thomas J Sweet
*Assistant Examiner* — Tiffany Shipmon
(74) *Attorney, Agent, or Firm* — Rader, Fishman & Grauer PLLC

(57) ABSTRACT

Provided is alloy for medical use and a medical device that is novel and useful. The alloy for medical use according to, for example, an embodiment of the present invention is mainly composed of three kinds of elements of gold (Au), platinum (Pt), and niobium (Nb). A total content of the three kinds of elements can be no smaller than 99% by weight, in which a platinum content can be no smaller than 5% by weight and no greater than 50% by weight and a niobium content can be no smaller than 3% by weight and no greater than 15% by weight. By adjusting the content ratio of the three elements, for example, it is possible to reduce or prevent artifacts in an MRI. Non-magnetization is also possible.

19 Claims, 19 Drawing Sheets

| Sample No. | Au (mass%) | Pt (mass%) | Nb (mass%) | MRI artifact |
|---|---|---|---|---|
| 1 | 91 | 5 | 4 | --- |
| 2 | 87 | 5 | 8 | None |
| 3 | 80 | 5 | 15 | ++ |
| 4 | 86 | 10 | 4 | --- |
| 5 | 82 | 10 | 8 | None |
| 6 | 75 | 10 | 15 | ++ |
| 7 | 75 | 15 | 10 | None |
| 8 | 73 | 15 | 12 | + |
| 9 | 71 | 15 | 14 | ++ |
| 10 | 75 | 20 | 5 | --- |
| 11 | 73 | 20 | 7 | − |
| 12 | 71 | 20 | 9 | None |
| 13 | 69 | 20 | 11 | None |
| 14 | 65 | 20 | 15 | ++ |
| 15 | 72 | 25 | 3 | --- |
| 16 | 70 | 25 | 5 | --- |
| 17 | 68 | 25 | 7 | − |
| 18 | 66 | 25 | 9 | None |
| 19 | 64 | 25 | 11 | ++ |
| 20 | 62 | 25 | 13 | ++ |
| 21 | 70 | 27 | 3 | --- |
| 22 | 68 | 27 | 5 | − |
| 23 | 66 | 27 | 7 | None |

(56) References Cited

FOREIGN PATENT DOCUMENTS

| JP | 2007-501658 A | 2/2007 |
|----|----|----|
| JP | 2007-267844 A | 10/2007 |
| WO | WO-00/61203 A1 | 10/2000 |
| WO | WO-2005/013856 A2 | 2/2005 |
| WO | WO-2007/089912 A2 | 8/2007 |
| WO | WO-2008/033711 A2 | 3/2008 |

OTHER PUBLICATIONS

International Preliminary Examination Report.

* cited by examiner

FIG.1

| Sample No. | Au (mass%) | Pt (mass%) | Nb (mass%) | MRI artifact |
|---|---|---|---|---|
| 1 | 91 | 5 | 4 | −− |
| 2 | 87 | 5 | 8 | None |
| 3 | 80 | 5 | 15 | ++ |
| 4 | 86 | 10 | 4 | −− |
| 5 | 82 | 10 | 8 | None |
| 6 | 75 | 10 | 15 | ++ |
| 7 | 75 | 15 | 10 | None |
| 8 | 73 | 15 | 12 | + |
| 9 | 71 | 15 | 14 | ++ |
| 10 | 75 | 20 | 5 | −− |
| 11 | 73 | 20 | 7 | − |
| 12 | 71 | 20 | 9 | None |
| 13 | 69 | 20 | 11 | None |
| 14 | 65 | 20 | 15 | ++ |
| 15 | 72 | 25 | 3 | −− |
| 16 | 70 | 25 | 5 | −− |
| 17 | 68 | 25 | 7 | − |
| 18 | 66 | 25 | 9 | None |
| 19 | 64 | 25 | 11 | ++ |
| 20 | 62 | 25 | 13 | ++ |
| 21 | 70 | 27 | 3 | −− |
| 22 | 68 | 27 | 5 | − |
| 23 | 66 | 27 | 7 | None |

FIG.2

| Sample No. | Au (mass%) | Pt (mass%) | Nb (mass%) | MRI artifact |
|---|---|---|---|---|
| 24 | 67 | 25 | 8 | None |
| 25 | 69 | 28 | 3 | — |
| 26 | 67 | 28 | 5 | — |
| 27 | 67 | 30 | 3 | — |
| 28 | 65 | 30 | 5 | — |
| 29 | 62 | 30 | 8 | None |
| 30 | 60 | 30 | 10 | + |
| 31 | 65 | 32 | 3 | —— |
| 32 | 60 | 32 | 8 | None |
| 33 | 58 | 32 | 10 | + |
| 34 | 60 | 35 | 5 | — |
| 35 | 57 | 35 | 8 | None |
| 36 | 55 | 35 | 10 | + |
| 37 | 58 | 37 | 5 | — |
| 38 | 55 | 40 | 5 | — |
| 39 | 52 | 40 | 8 | None |
| 40 | 50 | 40 | 10 | + |
| 41 | 42 | 50 | 8 | None |

FIG.5

| Sample No. | Wight (g) | Homogenized Heat Treatment | Vickers Hardness | R.P. (500°C) | R.P. (700°C) |
|---|---|---|---|---|---|
| 2 | 3.7943 | 1000°C × 8hr | 167 | △ | ○ |
| 5 | 3.7392 | 1000°C × 8hr | 190 | △ | ○ |
| 7 | 3.8451 | 1100°C × 8hr | 155 | ○ | |
| 8 | 3.9248 | 1100°C × 8hr | 248 | △ | |
| 12 | 3.790 | 1000°C × 8hr | 111 | | |
| 13 | 4.006 | 1000°C × 8hr | 214 | △ | |
| 17 | 4.0586 | 1000°C × 8hr | 119 | ○ | |
| 18 | 1.8576 | Not performed | 161 | ○ | |
| 22 | 1.8198 | Not performed | 80 | | |
| 23 | 2.0233 | Not performed | 79 | ○ | |
| 24 | 3.7370 | 1000°C × 24hr | 110 | ○ | ○ |
| 25 | 4.0594 | 1000°C × 24hr | 143 | | ○ |
| 26 | 3.9414 | 1000°C × 24hr | 153 | | ○ |
| 27 | 3.7969 | 1000°C × 24hr | 152 | | ○ |
| 28 | 4.0830 | 1000°C × 24hr | 122 | | ○ |
| 29 | 3.9616 | Not performed | 159 | | ○ |
| 32 | 3.9025 | Not performed | 95 | | ○ |
| 35 | 3.6668 | Not performed | 107 | | ○ |
| 39 | 3.8919 | Not performed | 153 | | ○ |

R.P. (Metal Rolling Property)
○ = Good
△ = Cracks appear around periphery

In images taken by the GE method,
a shape of the sample itself and an acrylic rod
for setting, the number of the black dots are
not become zero.

| Sample No. | (mass%) | | | artifact sizes | |
|---|---|---|---|---|---|
| | Au | Pt | Nb | SE (dot) | GE (dot) |
| 1 | 91 | | 4 | 407 | 10404 |
| 2 | 87 | 5 | 8 | 0 | 4003 |
| 3 | 80 | 5 | 15 | 556 | 13994 |
| 4 | 86 | 10 | 4 | 1120 | 9643 |
| 5 | 82 | 10 | 8 | 0 | 2298 |
| 6 | 75 | 10 | 15 | 388 | 13994 |
| 7 | 75 | 15 | 10 | 0 | 4208 |
| 8 | 73 | 15 | 12 | 152 | 12188 |
| 9 | 71 | 15 | 14 | 1479 | 12337 |
| 10 | 75 | 20 | 5 | 191 | 9265 |
| 11 | 73 | 20 | 7 | 85 | 5493 |
| 12 | 71 | 20 | 9 | 0 | 3012 |
| 13 | 69 | 20 | 11 | 0 | 5884 |
| 14 | 65 | 20 | 15 | 399 | 15715 |
| 15 | 72 | 25 | 3 | 692 | 12461 |
| 16 | 70 | 25 | 5 | 531 | 10426 |
| 17 | 68 | 25 | 7 | 119 | 8506 |
| 18 | 66 | 25 | 9 | 0 | 1796 |
| 19 | 64 | 25 | 11 | 64 | 4238 |
| 20 | 62 | 25 | 13 | 142 | 5286 |
| 21 | 70 | 27 | 3 | 440 | 3500 |
| 22 | 68 | 27 | 5 | 116 | 2429 |
| 23 | 66 | 27 | 7 | 0 | 4126 |
| 24 | 67 | 25 | 8 | 19 | 7144 |
| 25 | 69 | 28 | 3 | 370 | 10998 |
| 26 | 67 | 28 | 5 | 471 | 9949 |
| 27 | 67 | 30 | 3 | 156 | 9725 |
| 28 | 65 | 30 | 5 | 456 | 8901 |
| 29 | 62 | 30 | 8 | 0 | 7407 |
| 30 | 60 | 30 | 10 | 103 | 5523 |
| 31 | 65 | 32 | 3 | 695 | 9831 |
| 32 | 60 | 32 | 8 | 0 | 4592 |
| 33 | 58 | 32 | 10 | 7 | 6230 |
| 34 | 60 | 35 | 5 | 929 | 7731 |
| 35 | 57 | 35 | 8 | 0 | 4309 |
| 36 | 55 | 35 | 10 | 167 | 6358 |
| 37 | 58 | 37 | 5 | 0 | 7274 |
| 38 | 55 | 40 | 5 | 156 | 5661 |
| 39 | 52 | 40 | 8 | 61 | 3454 |
| 40 | 50 | 40 | 10 | 311 | 7353 |
| 41 | 42 | 50 | 8 | 10 | 6117 |

| Sample No. | Vickers hardness after the heat treatment (550 × 5 hours) | Vickers hardness after the heat treatment (700 × 30 minutes) |
|---|---|---|
| 2 | 180 (↑) | 221 (↑) |
| 5 | 190 (→) | 212 (↑) |
| 7 | 194 (↑) | |
| 8 | 256 (↑) | 271 (↑) |
| 13 | 211 (→) | 214 (→) |
| 18 | 188 (↑) | 182 (↑) |
| 23 | 75 (→) | 66 (↓) |
| 23 | 75 (→) | 66 (↓) |
| 23 | 75 (→) | 66 (↓) |
| 23 | 75 (→) | 66 (↓) |
| 23 | 75 (→) | 66 (↓) |

↑ = Hardness increased after heat treatment
→ = No change in hardness after heat treatment
↓ = Hardness decreased after heat treatment

| Sample | rod-shaped test piece χ (ppm) | rod-shaped test piece Δχ (ppm) | plate-shaped test piece χ (ppm) | plate-shaped test piece Δχ (ppm) | Magnetic susceptibility judged by MRI image | Artifact Sizes (SE) | Artifact Sizes (GE) |
|---|---|---|---|---|---|---|---|
| Au(known) | -34 | | | | — | | |
| Au-10Pt | -36 | -25 | | | | | |
| Au-20Pt | -23 | -27 | | | | | |
| Au-28Pt | -13 | -14 | | | — | | |
| Au-35Pt | 13 | -4 | | | ± | | |
| | | 22 | | | | | |
| Au-5Pt-4Nb | -22 | -13 | | | — | 407 | 10404 |
| Au-10Pt-4Nb | -22 | -13 | | | — | 1120 | 9643 |
| Au-5Pt-8Nb | -8 | 1 | -9 | 0 | ± | 0 | 4003 |
| Au-10Pt-8Nb | -8 | 1 | -10 | -1 | ± | 0 | 2298 |
| Au-15Pt-10Nb | -3 | 6 | -9 | 0 | + | 0 | 4208 |
| Au-5Pt-12Nb | 2 | 11 | | | | | |
| Au-20Pt-11Nb | | | -1 | 8 | ± | 0 | 5884 |
| Au-25Pt-8Nb | | | -13 | -4 | ± | 19 | 7144 |
| Au-25Pt-9Nb | | | | | ± | 0 | 1796 |
| Au-27Pt-7Nb | | | -10 | -1 | ± | 0 | 4126 |
| Au-30Pt-8Nb | | | | | ± | 0 | 7407 |
| Au-32Pt-8Nb | | | -10 | -1 | ± | 0 | 4592 |
| Au-35Pt-8Nb | | | -10 | -1 | ± | 0 | 4309 |
| Au-40Pt-8NB | | | -6 | 3 | ± | 61 | 3454 |
| Au-50Pt-8Nb | | | | | ± | 10 | 6117 |

⊠ means no plan of measurements

FIG.19

ALLOY FOR MEDICAL USE AND MEDICAL DEVICE

TECHNICAL FIELD

The present invention relates to an alloy for medical use and a medical device.

BACKGROUND ART

Recently, diagnoses using magnetic resonance imaging (MRI) have been broadly employed in the medical field. It is commonly known that a non-magnetic material is preferable for MRI. Further, performing a surgical operation under the magnetic field of MRI has become more common, and therefore non-magnetization of surgical implements is in demand.

In addition, it is also commonly known that a metallic material in the human body results in metal artifacts in MRI. While the metal artifacts do not generate signals in a site where the metallic material is present, single or double gradation is shown in a region adjacent to this site, and the metal artifacts cause geometric distortion in tissues that are drawn.

CITATION LIST

Patent Documents

Patent Document 1: Japanese Unexamined Patent Application Publication (Translation of PCT Application) No. 2004-505651
Patent Document 2: Japanese Unexamined Patent Application Publication No. 2007-267844
Patent Document 3: Japanese Unexamined Patent Application Publication (Translation of PCT Application) No. 2008-521567

DISCLOSURE OF THE INVENTION

Technical Problem

Documents such as Patent Document 1 and Patent Document 2 disclose using an alloy containing such as gold (Au) and platinum (Pt) as metallic materials having high biocompatibility and high MRI adequateness. These patent documents both include the description regarding the MRI adequateness, but a criterion on which the MRI adequateness is judged is not clear. In addition, examples of metallic medical devices that can be exposed to the MRI diagnosis while present in a human body include various devices such as stents, coils, and aneurysm clips. However, physical characteristics (hardness, strength, elasticity, workability, and such) required for some devices are different from other devices, and there is no proper alloy for medical use that can be applicable for reducing or preventing of artifacts in versatile purposes.

Further, when using the MRI, various methods can be used, such as the spin echo method and the gradient echo method, and using the spin echo method is commonly recommended when metal artifacts become a problem. However, as it is necessary to use the gradient echo method in angiography (MRA) or such, the reduction of artifacts in the gradient echo method is also demanded.

The present invention is made in view of the above problems, and an object of the present invention is to provide an alloy for medical use that can be applied to various medical devices, as well as a medical device.

Solution to Problem

To address the above problems, an alloy for medical use according to the present invention is mainly composed of three kinds of elements of gold (Au), platinum (Pt), and niobium (Nb).

As used herein, the phrase "mainly composed of" ("consisting essentially of" in claims) means, if there is a contamination of trace impurities (may be inevitable), or an addition of other elements, for example, oxide of metals, or a few other elements, may be included within the scope of this invention. Possible kind or ratio of impurity may be determined based on common general technical knowledge, but a ratio of impurity, such as oxide, can be nearly estimated to be 1 mass % at a maximum. Depending on the ratio of the three kinds of elements, there is revealed a possibility of various physical characteristics while reducing artifacts in MRI. However, there is a case in which it is possible to use an alloy having a ratio with which it is not possible to reduce MRI artifacts or prevent the artifacts from occurring as an alloy for medical use.

The inventors have first studied a binary alloy of gold (Au) and platinum (Pt). It is conventionally known that magnetic susceptibility of gold is negative, and magnetic susceptibility of platinum is positive, and mixing these two at a predetermined ratio to prepare an alloy realizes non-magnetization. However, the binary alloy cannot be applied to various medical devices in versatile purposes in terms of physical characteristics such as strength and hardness.

Therefore, the inventors further studied and found a possibility that adding niobium (Nb) as a third element, and controlling such as a composition and a manufacturing process realizes various physical characteristics (hardness, metal rolling property, and such) reducing artifacts.

As described in detail below, the ratio of the elements of a ternary alloy of the invention according to the present application that realizes a nonmagnetic property is such that a range of a ratio of niobium (Nb) is defined when a ratio of platinum (Pt) is a certain value, and by contrast a range of a ratio of platinum (Pt) is defined when a ratio of niobium (Nb) is a certain value. Further, it is found that increasing the ratio of a platinum (Pt) content exhibits an effect of artifact reduction when the ratio of niobium (Nb) is nearly 8% by weight (in this application, "% by weight" means "mass %"), and phase III signals appear in XRD analysis data when the ratio of the platinum (Pt) content is large. It can be considered from the above findings that there are numerous examples of the composition of the three kinds of elements that can realize the nonmagnetic property. A range in which reduction of artifacts is realized is even wider. Even with consideration of the trace impurities such as metal oxide that generate in melting of the three elements, it can be considered that a total of contents of the three elements is no smaller than 99% by weight.

However, the scope of the invention according to the present application is not limited to the above examples, and a different element, such as a fourth element or a fifth element, for example, can be added within the scope in which the reduction of artifacts (or non-magnetization) is realized. Addition of a different element other than the three elements can be studied in the future development of products having higher practical effects. As a specific example of the fourth element, the inventors confirmed that adding rhodium (Rh) by 1% by weight causes no artifact. If the ratio of the three elements is no smaller than 95% by weight, it may be considered that this is within the scope of the invention according to the present application. A case that is specifically confirmed is the case in which 1% by weight of rhodium (Rh) as the fourth element is added with consideration of the inclusion of the trace impurities. In this case, the total of the content ratio of the three kinds of elements is no smaller than 98% by weight, approximately. When the fourth element is not intentionally added, the total of the content ratio of the three kinds of elements is no smaller than 99% by weight with consideration of the inclusion of the trace impurities.

As described above, according to the description of the present application, the scope of being "consisting essentially of" the three kinds of elements is considered to be a case in which the total of the content ratio of the three kinds of elements is no smaller than 95% by weight in the case where the range is widely construed, and no smaller than 99% by weight when any different element is not intentionally added. The meaning of the phrase "mainly composed of" ("consisting essentially of" in claims) the three kinds of elements should be appropriately construed based on common general technical knowledge, in addition to the above description.

Patent Document 1 suggests using niobium as an additive. However, this is intended for improving mechanical characteristics, and as determined from the description that "more preferably from 1 to 5% by weight", there is virtually no disclosure regarding the reduction of artifacts or the non-magnetization (embodiment neither discloses a niobium-added alloy). Specifically, unlike the invention according to the present application, there is no suggestion regarding the realization of the reduction of artifacts with the ratio of niobium (Nb) in combination with the ratio of platinum (Pt), or the non-magnetization (artifacts do not occur). Patent Document 2 does not disclose even an idea of adding niobium.

Advantageous Effects of Invention

The alloy for medical use according to the present invention provides an advantageous effect of allowing an application to various medical devices such as stents, coils, and clips by appropriately selecting composition of elements and a manufacturing process when a ratio of the three elements is appropriately adjusted, while maintaining properties of reduction or prevention of artifacts in the MRI. However, as described above, the scope of the present invention is not limited to the scope in which the artifacts can be reduced or prevented from occurring. On the other hand, it is possible to obtain an advantageous effect that by using a nonmagnetic alloy for medical use, it is possible to reduce the artifacts (or prevent the artifacts from occurring) when a magnetic field is stronger, for example. As used herein, the "nonmagnetic" alloy for medical use means that magnetic susceptibility of the alloy itself is close to 0, or that a difference from magnetic susceptibility of water (−9 ppm) ($\Delta\chi$) is close to 0. More specifically, when an absolute value of the magnetic susceptibility of the alloy itself is no greater than 24 ppm, or when the absolute value of $\Delta\chi$ is no greater than 15 ppm, it is possible to obtain an alloy for medical use that is highly MRI-adequateness. It should be noted that the alloy for medical use according to the present invention is also superior in X-ray imperviableness.

BRIEF DESCRIPTION OF THE DRAWINGS

FIG. 1 is a table showing an examination result of MRI artifacts for alloy for medical use according to embodiments of the present invention.

FIG. 2 is a table showing an examination result of MRI artifacts for alloy for medical use according to embodiments of the present invention.

FIG. 5 is a table showing an examination result of Vickers hardness and metal rolling property of samples for which artifacts are not detected and samples for which artifacts are reduced and substantially not detected.

FIG. 16 is a table showing a list of the calculated artifact sizes.

FIG. 17 is a table showing a result of measuring Vickers hardness of the samples after an aging heat treatment.

FIG. 19 is a table for explaining magnetic susceptibility that has been measured.

BEST MODE FOR CARRYING OUT THE INVENTION

Hereinafter, an embodiment according to the present invention is described with reference to the drawings.

Figure 3:
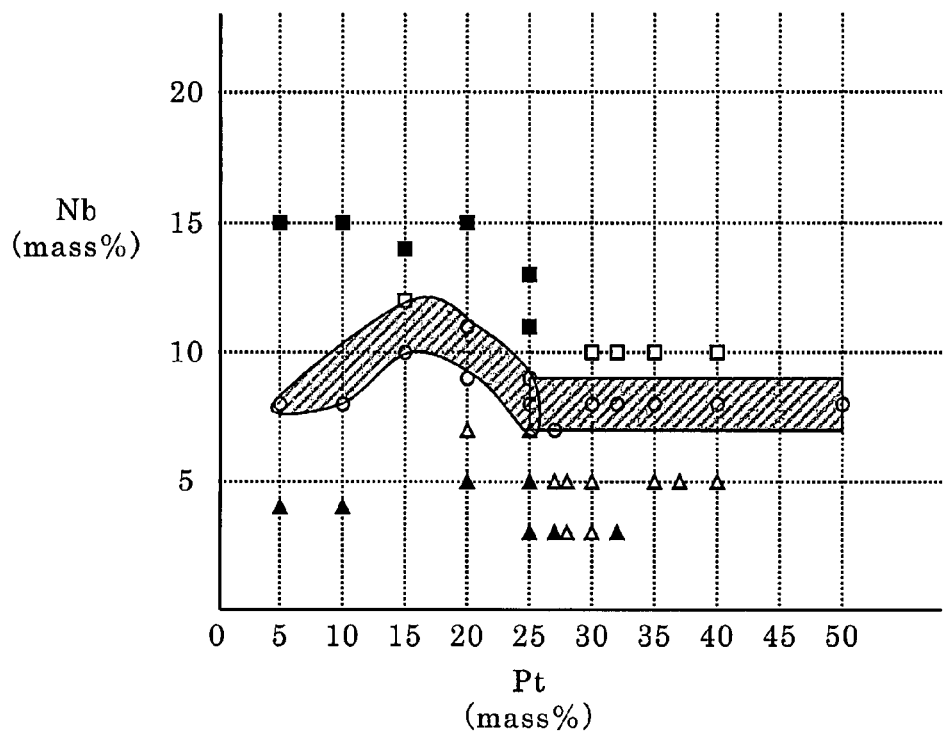
FIG. 3 is a chart graphically representing the examination results shown in FIG. 1 and FIG. 2.

The inventors have found the possibility that adding niobium (Nb) to gold (Au) and platinum (Pt) realizes various physical characteristics with reducing artifacts in MRI (or prevents artifacts from occurring). However, considering an application to a usage other than MRI, this does not necessarily mean to limit to the range that reduces artifacts in MRI (or prevents the artifacts from occurring). The following describes results of MRI measurement by changing a ratio of the three elements. FIG. 1 and FIG. 2 are tables showing ratios of the three elements in an alloy for medical use and examination results of MRI artifacts for alloys that the inventors have studied. FIG. 3 is a chart graphically representing the examination results by the inventors.

It should be noted that the samples were produced using gold (Au) manufactured by TANAKA KIKINZOKU KOGYO K.K. (purity of 99.99%), platinum (Pt) manufactured by TANAKA KIKINZOKU KOGYO K.K. (purity of 99.98%), and niobium (Nb) manufactured by the Nilaco Corporation (purity of 99.9%). Accordingly, in terms of the purity of raw materials, the purity of a total content of the three kinds of elements in any of the above samples is no smaller than 99.9% by weight. However, considering trace impurities such as metal oxide occurring in melting and such (considered to be 1% by weight at a maximum), the total content of the three kinds of elements can be considered to be no smaller than 99% by weight. Further, it would be also possible to add a different element, such as a fourth element or a fifth element, without departing from the scope of the spirit of reducing MRI artifacts or preventing artifacts from occurring (non-magnetization). As a specific example of the different element, the inventors have confirmed that adding rhodium (Rh) by 1% by weight does not affect the artifacts. Although addition of other elements can be studied in the future development of products having higher practical effects, it is considered that this is within the scope of the invention according to the present application if the ratio of the three elements is no smaller than 95% by weight. A case that has been specifically confirmed by the inventors is the case in which 1% by weight of rhodium (Rh) is added as an impurity. In this case, the total of the content ratio of the three kinds of elements is no smaller than 98% by weight. Broadly, the phrase "mainly composed of" ("consisting essentially of" in claims) can be defined, if the total ratio of the three elements is no smaller than 95% by weight. Or if the total ratio of the three elements is no smaller than 98% by weight. When only the three elements are mixed as raw materials, it is defined to be within the scope of being "mainly composed of" according to the present invention with considering trace impurities.

Figure 4:
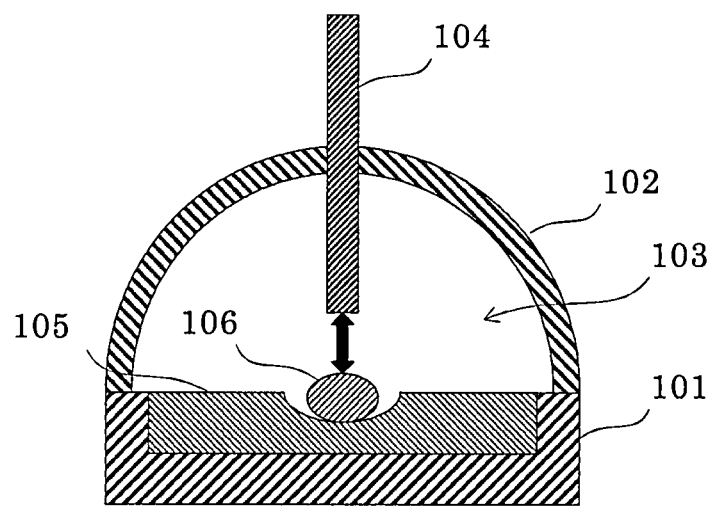
FIG. 4 is a view illustrating a schematic configuration of an argon arc melting furnace with which alloy samples according to embodiments are produced.

Each sample was produced based on argon arc melting such that the weight of an ingot of the produced alloy is about 4 grams (about 2 grams for samples No. 18, 22, and 23). FIG. 4 is a view schematically illustrating an entire configuration of an argon arc melting furnace with which the alloy samples according to this embodiment are produced.

The argon arc melting furnace used in this embodiment is configured such that a board 101 and a semispherical cover 102 are closely attached and a discharge space 103 is formed between the board 101 and the semispherical cove 102. An electrode 104 penetrates through the cover 102 while closely attached to the cover 102, a discharge occurs between a copper hearth 105 disposed within the board 101 and material metals placed on a recess in the copper hearth 105 and the electrode 104 to cause melting of the material metals, and whereby an alloy ingot sample 106 is produced. Here, the copper hearth 105 is being cooled by water so that the copper hearth 105 itself does not melt due to the heat in the discharge.

When producing the alloy ingot, the copper hearth 105 is slid outside, the material metals are placed on the recessed portion, the copper hearth 105 is returned to the original position, and then the discharge space 103 is vacuumized (on the order of $10^{-4}$ Pa). Next, argon-hydrogen mixed gas (hydrogen concentration of 1%) is introduced into the discharge space 103 to set an atmosphere within the space about 0.8 atmospheres.

Then, the discharge occurs between the electrode 104 and the material metals, whereby the material metals are melted. A discharge current is set about from 60 to 100 A. The duration of one discharge is set about from 20 to 30 seconds. After the discharge, melted metal is spontaneously-cooled. Heat mainly escapes to the copper hearth 105 that is cooled by water, and a part of heat is considered to be transferred to the argon-hydrogen mixed gas and a wall of the melting furnace. Time until a surface of ingot is coagulated depends on the weight of ingot, but is generally no longer than 1 second, and time until a red color of the surface disappear is no longer than about 2 seconds.

After one cycle of melting and coagulation is completed, the ingot is turned upside down, and subjected to a next cycle of melting and coagulation. This is a step for producing the ingot that is uniformly melted, and according to this embodiment, 10 cycles of melting and coagulation are carried out. After the 10 cycles of melting and coagulation are completed, a sample is taken out. The alloy samples homogenized heat treatment is "Not performed" as described in FIG. 5, the ingot area taken out here. In the case where samples are subjected to homogenized heat treatment, the conditions of treatment are described in FIG. 5. This is a step for uniformly causing the trace impurities dispersed in ingot samples.

When carrying out homogenized heat treatment, first, alloy ingot sample is inserted into a silica tube (outer diameter 15 mm, through-thickness 1 mm) and the silica tube is evacuated and vacuumized (on the order of $10^{-2}$ Pa). The silica tube is sealed while maintained as a vacuum, and the silica tube in which the ingot is contained is maintained to be in a vacuum state. Then, the silica tube in which the ingot is contained is placed in an electric furnace that is set to be 1000° C. or 1100° C., and maintained therein for a set duration of time (8 hours, for example, in this embodiment).

The silica tube is taken out from the electric furnace, and immersed in iced water to rapidly cool the silica tube. At this time, the silica tube is cooled while maintained as a vacuum without breaking the silica tube (in this embodiment, the silica tube is immersed in water so as not to break the silica tube in order to prevent oxidation of the ingot). After the cooling, the silica tube is broken to take out the ingot. It should be noted that the inventors have analyzed a part of ingots under an XRD analysis and confirmed that both Pt and Nb are phase II or phase III in most of the samples other than the samples with concentration of both Pt and Nb are low. Therefore, it is considered that the homogenized heat treatment is not a solution heat treatment (a heat treatment for the composition of the alloy being monolayer structure). A result of the XRD analysis will be later described in detail. The results shown in FIG. 1 and FIG. 2 are of an artifact evaluation after the homogenized heat treatment for the samples that are subjected to the homogenized heat treatment.

The presence of the MRI artifacts in the samples thus produced is confirmed by visual observation by pouring water into an acrylic container whose diameter is 5 cm and height is 5 cm, placing the alloy samples as large as a little finger in the water, and taking images of the samples using an MRI device (Magnetom Vision 1.5T manufactured by Siemens).

A direction of the artifacts becomes opposite depending on whether the magnetic susceptibility is positive or negative, and "no artifact" in FIG. 1 and FIG. 2 indicates that no artifact is detected. A "+" symbol indicates that some artifacts are detected in the direction of the positive magnetic susceptibility, and a "++" symbol indicates that the artifacts are detected in the direction of the positive magnetic susceptibility somewhat stronger than the case of "+". A "−" symbol indicates that some artifacts are detected in the direction of the negative magnetic susceptibility, and a "−−" symbol indicates that the artifacts are detected in the direction of the negative magnetic susceptibility somewhat stronger than the case of "−". However, as will be described later, the artifact evaluation of "+" and "−" indicate that the artifacts are sufficiently low. Considering Vickers hardness and metal rolling property as will be later described, it is considered that the application to the various medical devices is possible while realizing low artifacts sufficient for practical use, if (X, Y) values are within a shaded area shown on a left side in FIG. 3, that is, an area enclosed by (5, 8), (10, 8), (15, 10), (20, 9), (25, 7), (25, 9), (20, 11), (15, 12), and (5, 8) when taking a platinum content (% by weight) for an x-axis and a niobium content (% by weight) for a y-axis.

Further, it is also considered that applications to various medical devices are possible while realizing low artifacts sufficient for practical use, if the (X, Y) values are within a shaded area shown on a right part in FIG. 3, that is, an area enclosed by (25, 9), (25, 7), (50, 9), and (50, 7). It is interesting that no artifact is found when niobium (Nb) content is 8%, even if platinum (Pt) content is increased.

Now, a result of an examination for Vickers hardness and metal rolling property of some of the samples is described. In FIG. 5, the result of Vickers hardness and the metal rolling property after the alloy samples are produced is described. A column for the "homogenized heat treatment" indicates temperature and time when the homogenized heat treatment is carried out after the three elements are coagulated after being heated and melted. The indication of "Not performed" means that the three elements are coagulated after being melted, and are not subjected to the homogenized heat treatment.

The Vickers hardness was measured at a load of 100 grams and load time of 30 seconds using MVK-E manufactured by Akashi (currently, Mitutoyo Corporation). Metal rolling property (500° C.) was tested such that the alloy sample was vacuum-encapsulated within a stainless pipe having a diameter of 15 mm and through-thickness of 0.5 mm, heated for 3-5 minutes at 500° C., and then subjected to a rolling treatment in a copper roller. While visually observing a rolling state of the alloy sample from outside the stainless pipe, the sample was taken out after repeating the metal rolling treatment for 30-40 times, and the metal rolling property was determined. In FIG. 5, a circle indicates that no crack or such was found in the rolled sample and the metal rolling property is favorable, and a triangle indicates that a slight crack is observed around the sample. A column of metal rolling property (700° C.) shows a result of determination when a heating temperature was 700° C.

It should be noted that, other than the sample No. 8, samples subjected to aging heat treatment that will be later described (see FIG. 17) are subjected to a metal rolling property test after the aging heat treatment (after the aging heat treatment at 700° C. for the samples that are subjected to the aging heat treatment at 700° C., and after the aging heat treatment at 550° C. for sample No. 7 that is only subjected to the aging heat treatment at 550° C.). For sample No. 8, the result of the metal rolling property test performed after the homogenized heat treatment at 1100° C. and before the aging heat treatment at 550° C. is shown. All of samples No. 24 and thereafter are subjected to the metal rolling property test before the aging heat treatment.

It should be noted that while sample No. 7 is also subjected to the metal rolling property test before the aging heat treatment at 550° C., the metal rolling property was the same as the case after the aging heat treatment. Sample No. 13 is also subjected to the metal rolling property test before the aging heat treatment at 550° C., but the metal rolling property was the same as the case after the aging heat treatment at 700° C.

Figure 6:
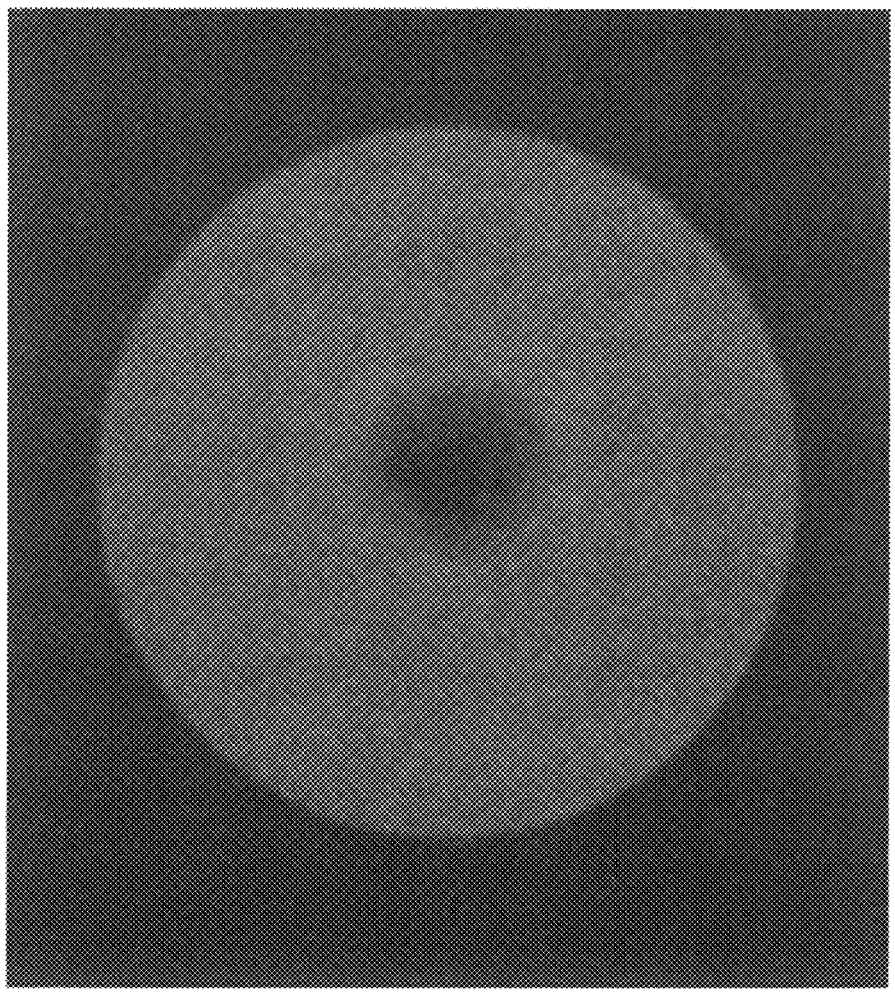
FIG. 6 is an MRI image of an alloy of a sample No. 7 (Pt 15%, Nb 10%) after being subjected to a homogenized heat treatment at 1100° C. for 8 hours after melting and solidification, taken by the turbo spin echo method (TR400, TE18).

Image data as results of actual measurements in MRI are shown. FIG. 6 is an MRI image of an alloy of sample No. 7 (Pt 15%, Nb 10%) after being subjected to the homogenized heat treatment at 1100° C. for 8 hours after melting and solidification. The image of FIG. 6 is taken by the turbo spin echo method (TR400, TE18). As can be seen from the figure, no artifact is detected.

Figure 7:
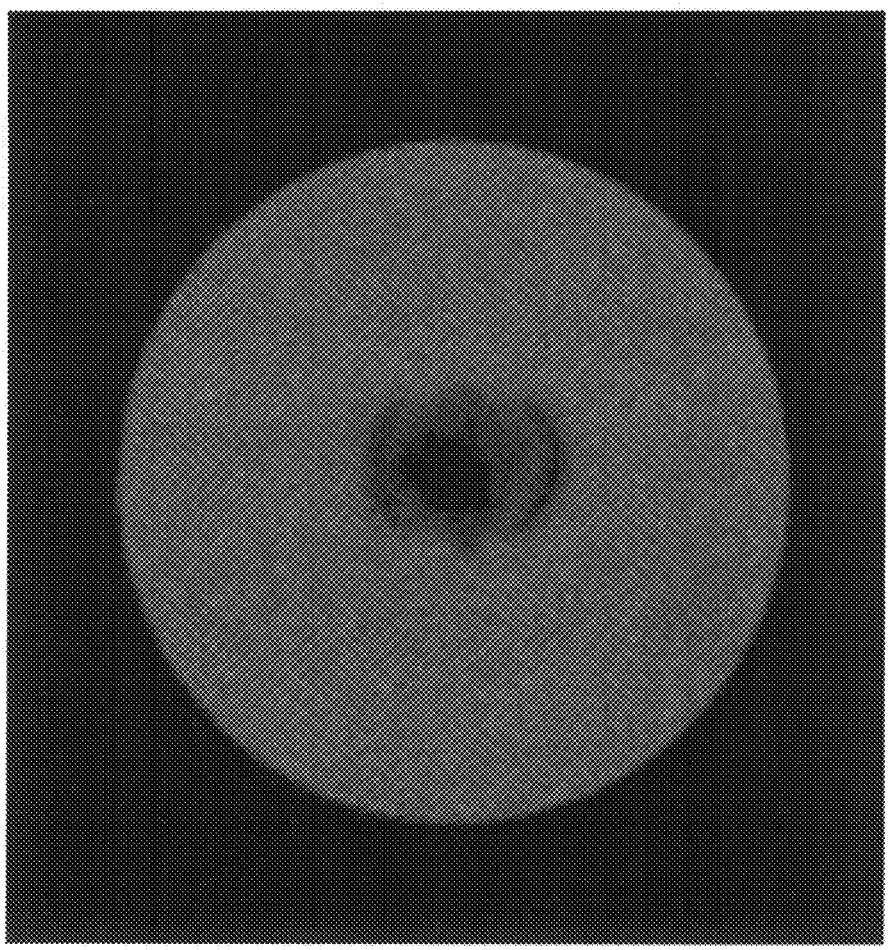
FIG. 7 is an MRI image of the alloy of the sample No. 7 (Pt 15%, Nb 10%) after being subjected to a homogenized heat treatment at 1100° C. for 8 hours after melting and solidification, taken by the gradient echo method (TR108, TE12).

FIG. 7 shows an example of the alloy of the same sample No. 7 (Pt 15%, Nb 10%) after being subjected to the homogenized heat treatment at 1100° C. for 8 hours after melting and solidification, taken by the gradient echo method (TR108, TE12). The gradient echo method is considered that artifacts tend to take place as compared to the spin echo method. However, as can be seen from the FIG. 7, no artifact is detected. As this sample has favorable metal rolling property, and the value of Vickers hardness can be increased up to a value no smaller than 180 by aging heat treatment as being described later. This sample can be used as an alloy for medical use that is effective in the angiography by the gradient echo method or when the intensity of the magnetic field is high. In addition, it is possible to expect applicability to medical devices such as clips for which pure titanium (Vickers hardness of around from 115 to 200) have been conventionally used. This also applies to the sample No. 18 (Pt 25%, Nb 9%). It should be noted that the images shown in FIG. 6 and FIG. 7 are taken before the aging heat treatment, but no artifact is detected after the aging heat treatment at 550° C.

Figure 8:
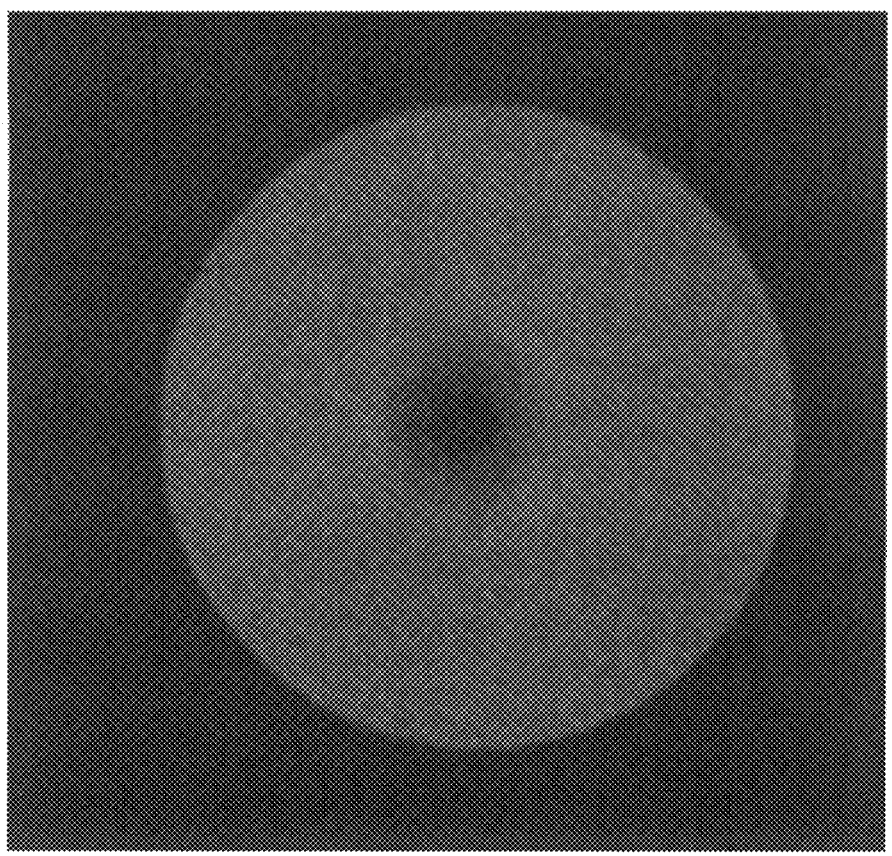
FIG. 8 is an MRI image of an alloy of a sample No. 8 (Pt 15%, Nb 12%) after being subjected to a homogenized heat treatment at 1100° C. for 8 hours after melting and solidification, taken by the turbo spin echo method (TR400, TE18).

Next, image data for examples of artifacts "+" are shown. FIG. 8 is an MRI image of the alloy of sample No. 8 (Pt 15%, Nb 12%) after being subjected to the homogenized heat treatment at 1100° C. for 8 hours after melting and solidification. The image of this figure is taken by the turbo spin echo method (TR400, TE18).

Figure 9:
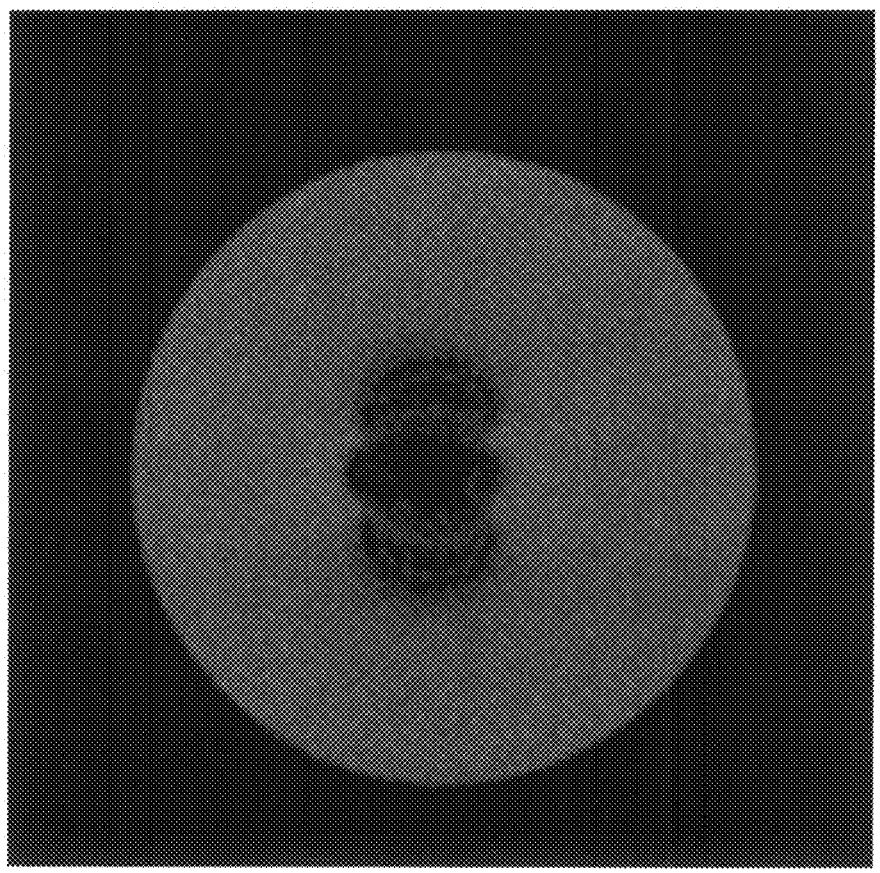
FIG. 9 is an MRI image of the alloy of the sample No. 8 (Pt 15%, Nb 12%) after being subjected to a homogenized heat treatment at 1100° C. for 8 hours after melting and solidification, taken by the gradient echo method (TR108, TE12).

FIG. 9 shows an example of the alloy of the sample No. 8 (Pt 15%, Nb 12%) after being subjected to the homogenized heat treatment at 1100° C. for 8 hours after melting and solidification, taken by the gradient echo method (TR108, TE12). The artifacts are sufficiently low even in the case of the artifact evaluation is "+". This sample has a high Vickers hardness 248, and it is expected to be applicable to the medical devices to which an alloy of platinum (Pt) 92% and tungsten 8% (on the order of Vickers hardness 245) has been conventionally used.

Figure 10:
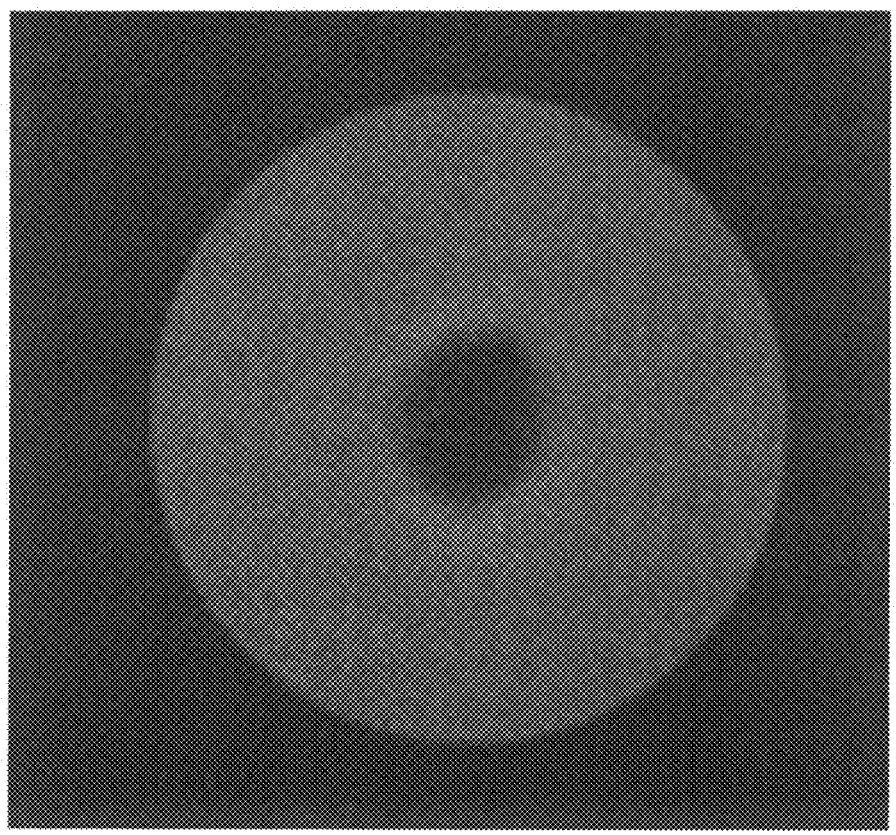
FIG. 10 is an MRI image of an alloy of a sample No. 17 (Pt 25%, Nb 7%) without any treatment after melting and solidification, taken by the turbo spin echo method (TR400, TE18).

Next, image data for examples of artifacts "−" are shown. FIG. 10 is an MRI image of the alloy of sample No. 17 (Pt 25%, Nb 7%) without any treatment after melting and solidification. The image of this figure is taken by the turbo spin echo method (TR400, TE18).

Figure 11:
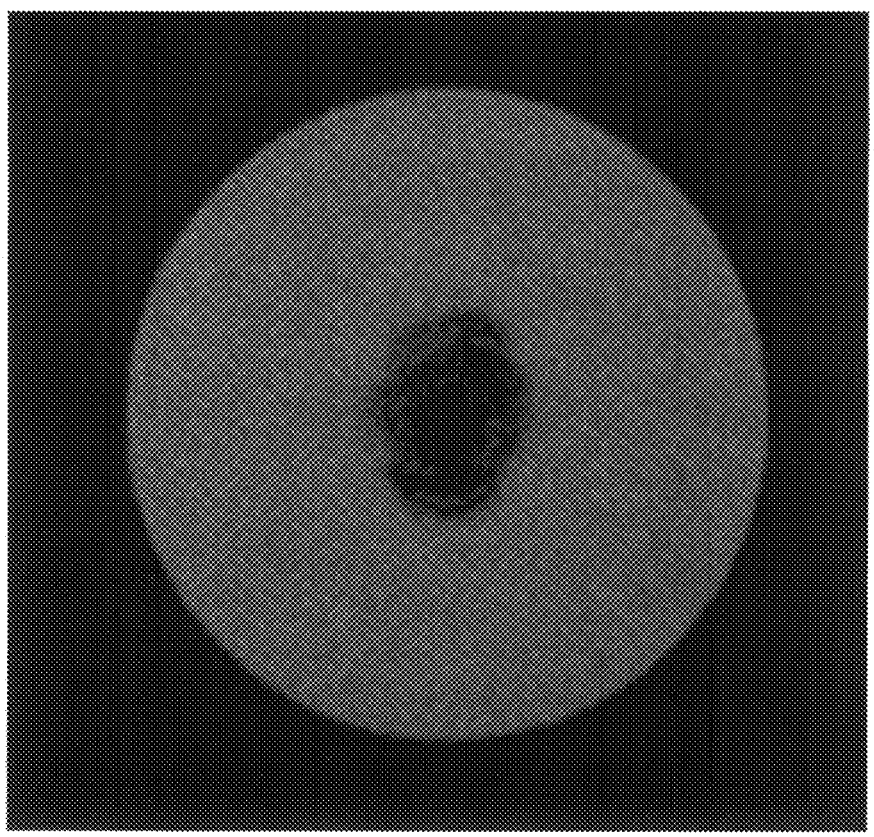
FIG. 11 is an MRI image of the alloy of the sample No. 17 (Pt 25%, Nb 7%) without any treatment after melting and solidification, taken by the gradient echo method (TR108, TE12).
Figure 12:
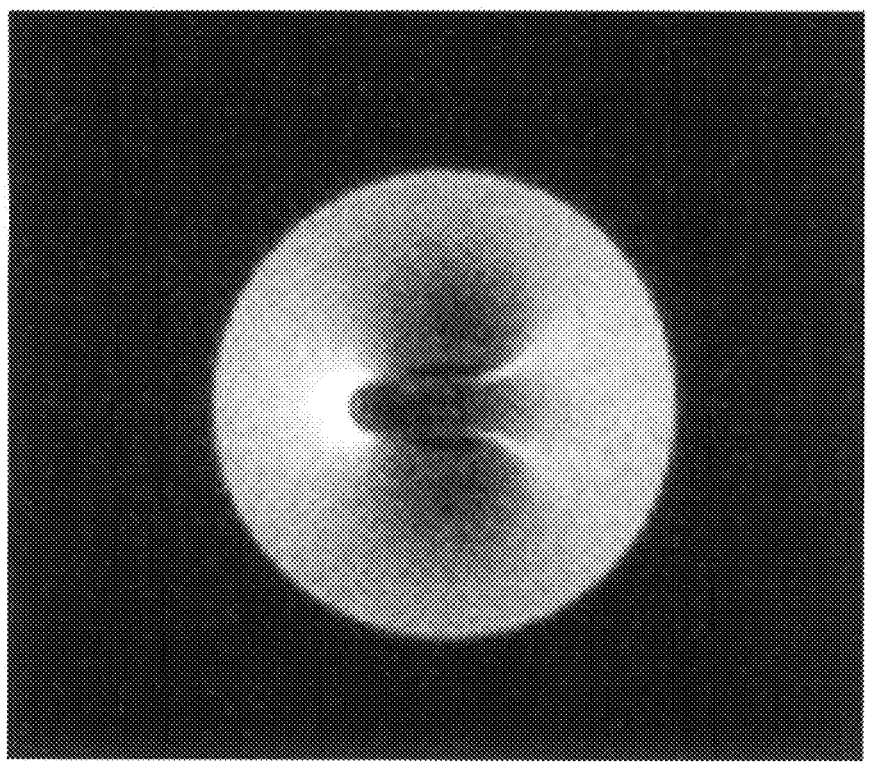
FIG. 12 is an MRI image of titanium (Ti) taken by the turbo spin echo method (TR500, TE12).
Figure 13:
FIG. 13 is an MRI image of titanium (Ti) taken by the gradient echo method (TR500, TE18).
Figure 14:
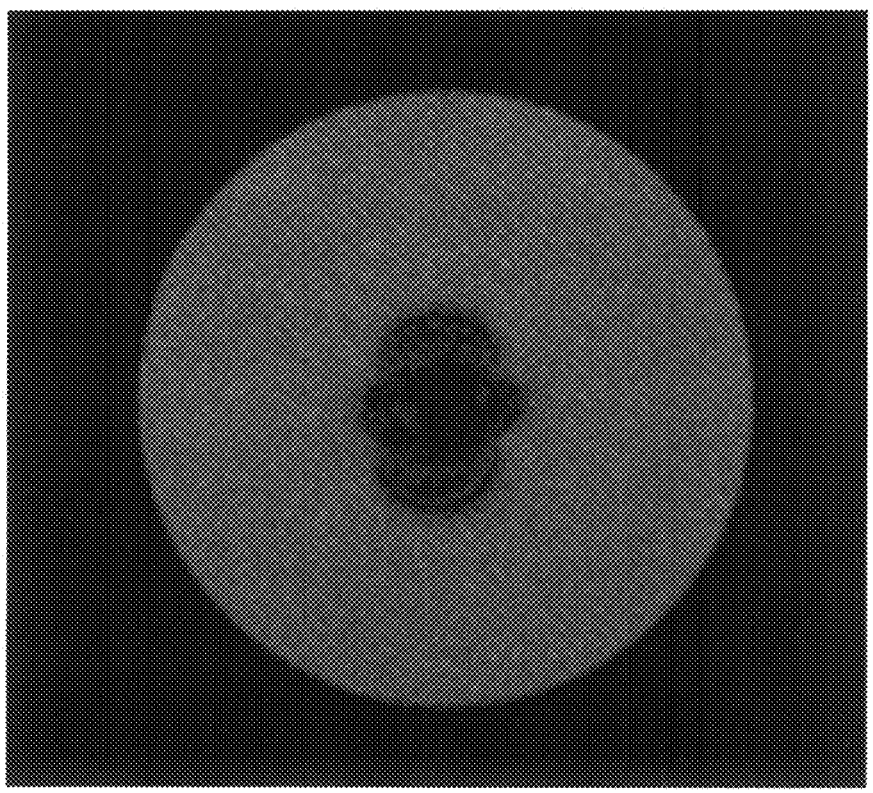
FIG. 14 is an MRI image of an alloy of a sample No. 16 (Pt 25%, Nb 5%), taken by the gradient echo method (TR108, TE12).

FIG. 11 shows an example of the alloy of sample No. 17 (Pt 25%, Nb 7%) without any treatment after melting and solidification, taken by the gradient echo method (TR108, TE12). As described above, the artifacts are enough reduced in either case of the artifact evaluation "+" or "−" in this embodiment. Here, MRI images of a sample formed of pure titanium (Ti) that are conventionally used as a material for clips are shown as comparison examples. FIG. 12 is an MRI image taken by the turbo spin echo method (TR500, TE12), and FIG. 13 is an MRI image taken by the gradient echo method (TR500, TE18). As compared to the conventional titanium, an effect of artifact reduction of the alloy for medical use according to these embodiments is apparent. It is additionally mentioned that according to embodiments of the present invention, the artifacts are sufficiently reduced even with an alloy whose artifact evaluation is "++" or "−−" as compared to conventional titanium. As an example, FIG. 14 shows an example of the alloy of sample No. 16 (Pt 25%, Nb 5%), taken by the gradient echo method (TR108, TE12).

Figure 15:
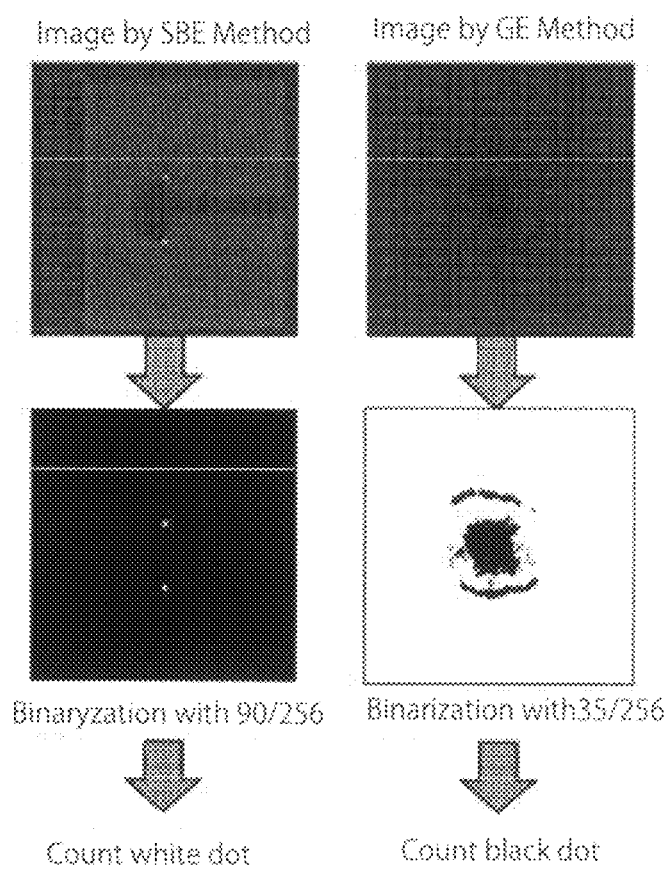
FIG. 15 is a diagram illustrating a method of quantification (calculation of artifact sizes).

In addition to image data exemplified above, the inventors have attempted quantification of an occurrence state of the artifacts. FIG. 15 is a diagram illustrating a method of quantification (calculation of an artifact size).

As shown in FIG. 15, in the calculation of the artifact size, an image taken by the turbo spin echo method (SE method) is binarized taking brightness 90 as a threshold value in 256 grey scale, and white dots in an image after the binarization process are counted for calculating the artifact size. Images taken by the gradient echo method (GE method) is binarized taking brightness 35 as a threshold value in 256 grey scale, and black dots in an image after the binarization process are counted for calculating the artifact size. It should be noted that, in images taken by the GE method, a shape of the sample itself and an acrylic rod for setting the sample are shown as black, and therefore the number of the black dots are not become zero as shown in this figure.

FIG. 16 is a table showing a list of artifact sizes thus calculated. It can be seen that this data generally matches the evaluation by visual observation shown in FIG. 1 and FIG. 2. Following shows imaging conditions under which the data shown in FIG. 15 is obtained in further detail. A static magnetic field intensity of both of the SE method and the GE method are 1.5 T. Effective visual fields of both of the SE method and the GE method are 75 cm×100 cm. A matrix of the SE method is 174×256 (dots), and a matrix of the GE method is 192×256 (dot), Slice thicknesses for both of the SE method and the GE method are set to 5 mm. TR/TE for the SE method is set to 400/18 (milliseconds). TR/TE of the GE method is set to 108/12 (milliseconds), an imaging time of the SE method is set to 1 minute 34 seconds, an imaging time of the GE method is set to 1 minute 25 seconds, and a flip angle in the GE method is 30 degrees.

Next, a result of the aging heat treatment performed to a part of the samples whose artifact evaluation is "None", "+," or "−", in an attempt to increase Vickers hardness, is described. FIG. 17 is a table showing a result of measuring Vickers hardness of the samples after the aging heat treatment.

"Vickers hardness after the heat treatment (550° C.×5 hours)" shown in this figure is Vickers hardness measured after 8 hours or 24 hours of homogenized heat treatment at 1000° C. or 1100° C. shown in FIG. 5, or after the aging heat treatment at 550° C.×5 hours without carrying out the homogenized heat treatment after melting and solidification. Further, "Vickers hardness after the heat treatment (700° C.×30 minutes)" is Vickers hardness measured after the aging heat treatment at 700° C.×30 minutes is carried out in order to realize further consolidation after the aging heat treatment at 550° C.×5 hours.

When the aging heat treatment is carried out, specifically, an alloy ingot is placed in a gas displacement electric furnace, and the gas displacement electric furnace is evacuated and vacuumized (on the order of $10^{-1}$ Pa). Then, argon gas is introduced into the electric furnace, and the electric furnace is heated up to a setting temperature (550° C. or 700° C.), and maintained for set time (5 hours or 30 minutes). The electric furnace is opened and the ingot is taken out of the electric furnace and rapidly cooled in iced water.

As shown in FIG. 17, Vickers hardness has increased in many cases, although there are the samples having little change in Vickers hardness due to the aging heat treatment like the sample No. 13, for example, and samples with decreased Vickers hardness due to the aging heat treatment like the sample No. 23. In a case of platinum (Pt) 27% by weight, the value of Vickers hardness is somewhat small, and it appears to be slightly unsuitable to the angiography for which the gradient echo method is suitably used. However, if Vickers hardness can be set to a value no smaller than 180, it may be suitable for applying to various medical devices such as stents and clips. For the aging heat treatment, an alloy for medical use that is more useful may be expected by further study. In the aging heat treatment shown in FIG. 17, the degree of the artifacts does not change in all of the samples, and it is shown that there is applicability to various medical devices by selecting the composition of the material metals and carrying out processes such as the aging heat treatment.

Figure 18:
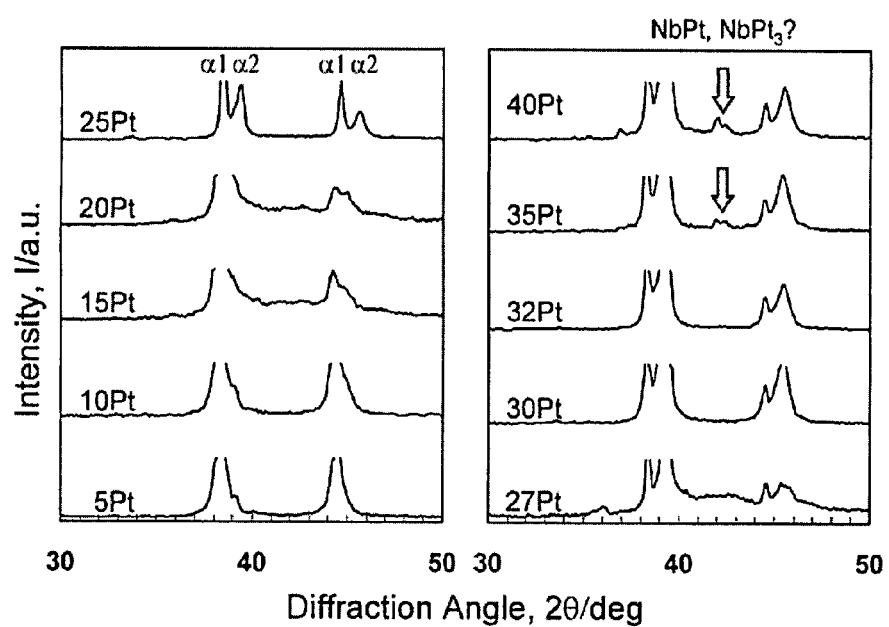
FIG. 18 is a chart showing a result of an XRD analysis for alloys that are determined to produce no artifact.

Here, the result of the XRD analysis for the alloy ingots as described above is described. FIG. 18 is a chart showing the result of the XRD analysis for the alloys that are determined to produce no artifact. All of the examples shown in the figure are ternary alloys of gold, platinum, and niobium. In this figure, "5Pt" is a result of "5Pt—8Nb (Pt 5% by weight, Nb 8% by weight, and the remaining—87% by weight is Au (may include the trace impurities, which is the same as other results listed below)), "10Pt" is a result of "10Pt—8Nb", "15Pt" is a result of "15Pt—10Nb", "20Pt" is a result of "20Pt—11Nb", "25Pt" is a result of "25Pt—8Nb", "27Pt" is a result of "27Pt—7Nb", "30Pt" is a result of "30Pt—8Nb", "32Pt" is a result of "32Pt—8Nb", "35Pt" is a result of "35Pt—8Nb", and "40Pt" is a result of "40Pt—8Nb".

The melted alloy ingot is subjected to the metal rolling treatment at 700° C. after the homogenized heat treatment or without the homogenized heat treatment, and then polished and used in the analysis. After the metal rolling treatment, neither annealing nor the aging heat treatment is performed.

It should be noted that the measurement conditions are: a CuKα beam (30 kV, 15 mA), a scanning speed is 0.5 degrees/minute, and a sampling width is 0.1 degrees. Also shown in FIG. 18, (1) in the sample with a low Pt ratio (5Pt, 10Pt), only α single phase is confirmed in the XRD diagram even without a melting treatment.

(2) When the Pt ratio increases (15Pt—32Pt), the phase II is seen in the XRD diagram, and separation into two phases of α1+α2 can be seen. In the case of 27Pt, noise may be included at this moment that a noise occurs as the sample test piece is small. However, a reason why such a result was obtained is unknown.

(3) When the Pt ratio further increases (35Pt, 40Pt), the phase III is seen in the XRD diagram. Intermetallics containing Pt and Nb have a number of phases showing a peak around this point, and therefore the appearing phase III is not identified. However, it is considered that a phase such as NbPt or $NbPt_3$ appears. Further, the peak also appears to include two different phases, and there is a possibility that a fourth phase and thereafter is included.

As can be seen from the data and findings described above, the magnetic susceptibility of the alloy according to these embodiments may not bea simple proportionate relation based only on the element ratio. For example, it may be considered that types and ratios of phases are involved, and that there is a possibility that the magnetic susceptibility changes when the types and the ratios of the phases change due to the heat treatment. From the view point of the fact that has been exampled, as long as the phase in the alloy is the phase a (face-centered cubic metal), it is considered that a degree of the change of the magnetic susceptibility due to the type and the ratio of the phases is small. However, it is highly probable that the intermetallic compound shown in FIG. 18 includes phases of different crystal systems, and a slight change of the ratio may change the magnetic susceptibility. For example, there is a possibility that the magnetic susceptibility changes due to a solution heat treatment and an aging heat treatment. Viewing the other way around, there is a possibility that the composition that is not nonmagnetic in the data obtained this time becomes nonmagnetic by being subjected to the heat treatment. It is also expected that the mechanical characteristic also changes at the same time, and therefore, there is a possibility that an alloy of the composition whose artifacts were not reduced or prevented this time becomes nonmagnetic by being subjected to the heat treatment, or may be nonmagnetic alloy showing different characteristics.

Further, a measurement result of the magnetic susceptibility of the alloys whose artifacts are reduced or prevented is described. FIG. 19 is a table for explaining the magnetic susceptibility that has been measured. The alloys used in the magnetic susceptibility measurement include alloys of the composition that is not shown in FIG. 1 and FIG. 2. However, a different element is not additionally added to any of these alloys, and only produced by the three elements of Au, Pt, and Nb. "Au—25Pt—8Nb" shown in FIG. 19 indicates that this sample includes Pt 25% by weight, Nb 8% by weight, and Au 67% by weight (although the trace impurities may be included).

The following describes a method of preparing the samples for the measurement of the magnetic susceptibility. In a case of a "rod-shaped test piece" as shown in FIG. 19, (1) the materials were weighed to realize a target composition, and melted in the arc melting furnace as exemplified in FIG. 4, and whereby an ingot of about 6 g was produced. (2) Using an argon atmosphere high-frequency induction heating casting machine Argoncaster-T (Shofu Inc., Kyoto), a rod-shaped test piece was made. A crucible used was T-Crucible (Shofu Inc.), and a casting mold material used for producing a casting mold is Ceravest Quick (GC Corporation, Tokyo). (3) A casting mold was produced to include a cavity having a diameter of about 3 mm and a length of about 25 mm, dried, and preheated at 800° C., and set in the casting machine. The crucible was also dried and preheated at 800° C., and set in the casting machine, and an ingot was placed in the crucible. After the casting process started, it was seen by visual observation that the ingot melted in argon an atmosphere, and the melted material was injected into the casting mold. (4) After the temperature was lowered in the argon atmosphere, the casting mold was taken out and sufficiently cooled down in water, and the casting mold was broken to take out a cast body. The casting mold and such attached to a surface of the cast body was removed by polishing. (5) A diameter of the rod-shaped test piece having a diameter of about 3 mm and a length of about 25 mm at each of portions about 8 mm from an end on both ends were measured 10 times using a caliper, and an average diameter of the both ends were calculated.

In the case of a "plate-shaped test piece", (1) the materials were weighed to realize a target composition, and melted in the arc melting furnace as exemplified in FIG. 4, and whereby an ingot of about 4 g was produced. (2) The ingot vacuum-encapsulated in a stainless pipe was rolled in entirety. The rolling was carried out by repeating a process of heating in an electric furnace at 700° C., rolling once, and then reheating. (3) After the rolling, the stainless pipe was opened and a plate-shaped alloy sample was taken out. A plate whose width is about 2 mm was cut out from the sample, a surface that has been in contact with the stainless pipe was grounded, and then a test piece was cut out such that the length of the test piece was no longer than 8 mm. The thickness of the test piece was about 1-2 mm. (4) Out of the test pieces, two or three test pieces that could be filled at the same time into a sample tube for measuring magnetic susceptibility were selected, and a total volume was measured using Densitometer Accupyc 1330 (Shimadzu Corporation, Kyoto).

As shown in FIG. 19, the magnetic susceptibility measurement is performed for both of a "rod-shaped test piece" and a "plate-shaped test piece" of a part of the alloys, and the results of the measurement of the two test pieces were similar for the samples other than the sample of Au—15Pt—10Nb. The reason why the measurement values of the two test pieces were different for the sample of Au—15Pt—10Nb may be that the uniformity of the composition of the sample is not guaranteed (the homogenized heat treatment is not performed).

The following describes the method of measuring the magnetic susceptibility and calibration of measured value data. For measuring volume magnetic susceptibility of the samples, a magnetic balance of MSB-AUTO (Sherwood Scientific, UK) was used. An inner diameter of a sample tube for measurement of this device is 3.24 mm, and the device outputs the magnetic susceptibility of the sample filled in a measurement space to a depth of about 8.5 mm (0.07 ml in volume). Therefore, when a test piece for measurement is not filled in this space, it is necessary to calibrate a measured value based on a volume of the test piece.

In a case of the rod-shaped test piece, it is not possible to directly measure a sample volume within the measurement space as the length of the test piece is no shorter than 8.5 mm, and therefore the calibration is carried out based on the diameter of the test piece. Where an average diameter of the test pieces is D mm and the measured value of the magnetic susceptibility is $\chi_0$, the calibrated magnetic susceptibility $\chi$ of the sample is expressed by an equation 1 shown below. Here, the measurement is carried out on both ends of the rod-shaped test piece, and an average of the measured values is taken as the magnetic susceptibility.

$$\chi = \chi_0 \times (3.24/D)^2 \tag{Equation 1}$$

In a case of the "plate-shaped test piece," as the length of the test piece is no longer than 8 mm, the calibration is carried out based on the volume. Where a total volume of the test piece is V ml and the measured value of the magnetic susceptibility is $\chi_0$, the magnetic susceptibility $\chi$ of the sample is expressed by an equation 2 shown below.

$$\chi = \chi_0 \times (0.07/V) \tag{Equation 2}$$

The artifacts of the magnetic susceptibility demonstrated by the metal present within a human body in MRI occurs due to a mismatch in the volume magnetic susceptibility between the metal and surrounding body tissues. Accordingly, in order to reduce or prevent the artifacts of the magnetic susceptibility, it is preferable that the magnetic susceptibility of the alloy is approximated by −9 ppm, which is the magnetic susceptibility of water that is nearly equal to the magnetic susceptibility of the body tissue. Depending on the application (for example, dental materials), it is preferable that the magnetic susceptibility of the alloy itself is close to 0. A value $\Delta\chi$ shown in FIG. 19 is a difference between the magnetic susceptibility of the alloy and the magnetic susceptibility of water, and the alloy can be preferable for medical use if an absolute value of $\Delta\chi$ is close to zero. This also applies to a case in which the magnetic susceptibility of the alloy itself is close to 0.

As described above, there was a case in which the measured values of the magnetic susceptibility on both ends of the "rod-shaped test piece" are different. However, a difference between the detected data of the magnetic susceptibility on the both ends is 4 ppm at a maximum. A maximum value of an absolute value of the magnetic susceptibility detected for an artifact free alloy is 24 ppm (−24 ppm for "5Pt—4Nb"), and a maximum value of an absolute value of the difference $\Delta\chi$ from the magnetic susceptibility of water is 15 ppm (−15 ppm for "5Pt—4Nb"). Such a nonmagnetic alloy is considered to be a favorable alloy for medical use that is not comparable with the technique disclosed in Patent Document 3, for example.

As described above, the artifacts of the alloy for medical use according to these embodiments in an MRI is prevented or reduced to almost none. In addition, the alloy for medical use according to these embodiments shows a possibility of realizing many kinds of characteristics that may be applied to various medical devices by adjusting the content of each element and carrying out the heat treatment and such.

Method of Medical Treatment Using Alloy for Medical Use According to Embodiments As described above, the ternary alloy for medical use according to these embodiments may realize many kind of characteristics, and may be applied to (1) stents, coils, and clips including aneurysm clips; (2) housings for an implantable artificial heart; (3) casings, electrodes, and terminals for a cardiac pacemaker; (4) artificial valve frames; and (5) various medical devices such as surgical implements that are used under an MRI environment. The usage of various medical devices can be considered in a similar manner to the conventional usage, and using the alloy for medical use according to this embodiment can provide medical devices having extremely high bio-adequateness and MRI adequateness. In particular, the alloy for medical use according to this embodiment may be suitably used in the gradient echo method.

INDUSTRIAL APPLICABILITY

The present invention can be applied to various medical devices such as stents, coils, and clips.

The invention claimed is:
1. Alloy for medical use consisting essentially of:
three kinds of elements of gold (Au), platinum (Pt), and niobium (Nb).
2. The alloy for medical use according to claim 1, wherein artifacts in MRI are reduced.
3. The alloy for medical use according to claim 1, wherein a total content of the three kinds of elements is no smaller than 99% by weight.
4. The alloy for medical use according to claim 1, wherein an element different from the three kinds of elements is added in a range that allows reduction of artifacts.
5. The alloy for medical use according to claim 4, wherein a total content of the three kinds of elements is no smaller than 98% by weight.
6. The alloy for medical use according to claim 1, wherein a total content of the three kinds of elements is no smaller than 95% by weight.
7. The alloy for medical use according to claim 1, wherein a platinum content is no smaller than 5% by weight and no greater than 27% by weight, and niobium content is no smaller than 3% by weight and no greater than 15% by weight.
8. The alloy for medical use according to claim 1, wherein a platinum content is no smaller than 5% by weight and no greater than 25% by weight, and niobium content is no smaller than 7% by weight and no greater than 12% by weight.
9. The alloy for medical use according to claim 1, wherein, within a compositional representation of the alloy on a Cartesian coordinate system with an x-axis is a platinum content (% by weight) and a y-axis is a niobium content (% by weight), the compositional representation includes an area enclosed by the following (X,Y) values: (5, 8), (10, 8), (15, 10), (20, 9), (25, 7), (25, 9), (20, 11), (15, 12), and (5, 8).
10. The alloy for medical use according to claim 1, wherein, within a compositional representation of the alloy on a Cartesian coordinate system with an x-axis is a platinum content (% by weight) and a y-axis is a niobium content (% by weight), the compositional representation includes an area enclosed by the following (X,Y) values: (25, 9), (25, 7), (50, 9), and (50, 7).
11. The alloy for medical use according to claim 1, wherein the alloy is not magnetically susceptible.
12. The alloy for medical use according to claim 1, wherein a platinum content of the alloy is no smaller than 5% by weight and no greater than 50% by weight, and a niobium content is no smaller than 7% by weight and no greater than 11% by weight.
13. The alloy for medical use according to claim 1, wherein an absolute value of magnetic susceptibility of the alloy is no greater than 24 ppm.
14. The alloy for medical use according to claim 1, wherein an absolute value of a difference from an absolute value of magnetic susceptibility of the alloy and a magnetic susceptibility of water (9 ppm) is no greater than 15 ppm.
15. The alloy for medical use according to claim 1, wherein Vickers hardness is no smaller than 180.
16. The alloy for medical use according to claim 15, wherein
Vickers hardness is set to be no smaller than 180 by melting and coagulating the three elements and carrying out an aging heat treatment to the three elements.
17. A medical device, comprising:
the alloy for medical use according to claim 1.
18. The medical device according to claim 17, wherein the medical device is one selected from (1) a stent, a coil, or a clip including an aneurysm clip, (2) a housing of an implantable artificial heart, (3) a casing, an electrode, or a terminal of a cardiac pacemaker, (4) an artificial valve frame, and (5) a surgical implement used under an MRI environment.
19. The medical device according to claim 17, wherein the medical device is used in angiography according to a gradient echo method.

* * * * *